(12) United States Patent
Spero et al.

(10) Patent No.: US 7,611,475 B2
(45) Date of Patent: Nov. 3, 2009

(54) ROTATIONAL CORE BIOPSY DEVICE WITH LIQUID CRYOGEN ADHESION PROBE

(75) Inventors: Richard K. Spero, Pleasanton, CA (US); Christopher D. Owen, Pleasanton, CA (US); Daniel V. Van Buskirk, Pleasanton, CA (US); Stephen L. Daleo, Dublin, CA (US); Russell L. DeLonzor, Pleasanton, CA (US)

(73) Assignee: Sanarus Technologies, LLC, Pleasanton, CA (US)

( * ) Notice: Subject to any disclaimer, the term of this patent is extended or adjusted under 35 U.S.C. 154(b) by 0 days.

(21) Appl. No.: 12/177,470

(22) Filed: Jul. 22, 2008

(65) Prior Publication Data

US 2008/0281225 A1    Nov. 13, 2008

Related U.S. Application Data (63) Continuation of application No. 10/779,520, filed on Feb. 12, 2004, now Pat. No. 7,402,140.

(51) Int. Cl.
  *A61B 10/02* (2006.01)
(52) U.S. Cl. .................. 600/568; 600/562; 600/567; 606/20; 606/23; 606/167
(58) Field of Classification Search ............... 600/562, 600/564–568, 584; 606/20–23, 167, 170, 606/180, 181, 185; 604/19, 22, 23, 164.01, 604/164.11
See application file for complete search history.

(56) References Cited

U.S. PATENT DOCUMENTS

| | | | |
|---|---|---|---|
| 4,644,951 | A | 2/1987 | Bays |
| 5,027,827 | A | 7/1991 | Cody et al. |
| 5,056,523 | A | 10/1991 | Hotchkiss, Jr. et al. |
| 5,056,532 | A | 10/1991 | Hull et al. |
| 5,133,360 | A | 7/1992 | Spears |
| 5,234,000 | A | 8/1993 | Hakky et al. |
| 5,353,804 | A | 10/1994 | Kornberg et al. |
| 5,649,547 | A | 7/1997 | Ritchart et al. |
| 5,769,086 | A | 6/1998 | Ritchart et al. |
| 5,775,333 | A | 7/1998 | Burbank et al. |
| 5,810,806 | A | 9/1998 | Ritchart et al. |

(Continued)

FOREIGN PATENT DOCUMENTS

WO    WO 97/20504    6/1997

(Continued)

OTHER PUBLICATIONS

G.S. Ferzli et al., Advanced Breast Biopsy Instrumentation: A Critique, Journal of American College of Surgeons; 1997; 185:145-151.

(Continued)

*Primary Examiner*—Ahmed M Farah
(74) *Attorney, Agent, or Firm*—Niky Economy Syrengelas, Esq.; Crockett & Crockett (57) ABSTRACT

A device for biopsy of body tissue. The device is driven by liquid CO2, and is provided with a control system to control various components to effectuate rotating core biopsies.

5 Claims, 6 Drawing Sheets

U.S. PATENT DOCUMENTS

| | | | |
|---|---|---|---|
| 5,833,685 A | 11/1998 | Tortal et al. | |
| 5,868,673 A | 2/1999 | Vesely | |
| 5,913,857 A | 6/1999 | Ritchart et al. | |
| 5,928,164 A | 7/1999 | Burbank et al. | |
| 5,944,673 A | 8/1999 | Gregoire et al. | |
| 5,964,716 A | 10/1999 | Gregoire et al. | |
| 6,007,497 A | 12/1999 | Huitema | |
| 6,017,316 A | 1/2000 | Ritchart et al. | |
| 6,277,083 B1 | 8/2001 | Eggers et al. | |
| 6,540,694 B1 * | 4/2003 | Van Bladel et al. | 600/564 |
| 6,551,255 B2 * | 4/2003 | Van Bladel et al. | 600/584 |
| 6,758,824 B1 | 7/2004 | Miller et al. | |
| 7,402,140 B2 * | 7/2008 | Spero et al. | 600/568 |
| 2007/0055173 A1 * | 3/2007 | DeLonzor et al. | 600/564 |

FOREIGN PATENT DOCUMENTS

| | | |
|---|---|---|
| WO | WO 98/06346 | 2/1998 |
| WO | WO 98/08441 | 2/1998 |
| WO | WO 99/44506 | 9/1999 |
| WO | WO 00/12009 | 3/2000 |

OTHER PUBLICATIONS

Edgar D. Staren, MD et al., Ultrasound-Guided Needle Biopsy of the Breast, Surgery; Oct. 1999, 629-625.

Parker et al., Performing a Breast Biopsy with a Directional, Vacuum-Assisted Biopsy Instrument, Radiographics; 1997 (Sep.-Oct.); 17(5):1233-52.

Jackman RJ et al., Needle-Localized Breast Biopsy: Why Do We Fail?, Radiology Sep. 1997, 204(3); 677-84.

Jackman RJ et al., Percutaneous Removal of Benign Mammographic Lesions: Comparison of Automated Large-Core and Directional Vacuum-Assisted Stereotactic Biopsy Techniques, AJR Am J Roentgenol Nov. 1998; 171(5), 1325-30.

Tyco Minimally Invasive Breast Biopsy.

Biopsy Mammotome Brochure.

Bard Product Brochure.

Breast Care Info Web Page: Steps in the Mammotome Procedure.

Open Excisional Surgical Biopsy: Breast Biopsy Website.

Stereotactics in Breast Biopsy: Breast Biopsy Website.

* cited by examiner

ROTATIONAL CORE BIOPSY DEVICE WITH LIQUID CRYOGEN ADHESION PROBE

This application is a continuation of U.S. application Ser. No. 10/779,520 filed Feb. 12, 2004 now U.S. Pat. No. 7,402,140.

FIELD OF THE INVENTIONS

The devices and methods described below relate to the diagnosis and treatment of breast lesions, and more generally, to the diagnosis and treatment of tumors and lesions throughout the body.

BACKGROUND OF THE INVENTIONS

Biopsy is an important procedure used for the diagnosis of patients with cancerous tumors, pre-malignant conditions, and other diseases and disorders. Typically, in the case of cancer, when the physician establishes by means of procedures such as palpation, mammography or x-ray, or ultrasound imaging that suspicious circumstances exist, a biopsy is performed. The biopsy will help determine whether the cells are cancerous, the type of cancer, and what treatment should be used to treat the cancer. Biopsy may be done by an open or percutaneous technique. Open biopsy, which is an invasive surgical procedure using a scalpel and involving direct vision of the target area, removes the entire mass (excisional biopsy) or a part of the mass (incisional biopsy). Percutaneous biopsy, on the other hand, is usually done with a needle-like instrument through a relatively small incision, blindly or with the aid of an imaging device, and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section. One important area where biopsies are performed is the diagnosis of breast tumors.

Traditionally, the biopsy technique for breast tumors involves placing a biopsy device multiple times into the breast and taking several samples of tissue from a mass or tumor which is suspected of being cancerous. Several samples are required to be sure that some tissue from the suspect mass has been captured, and enough tissue has been sampled to ensure that, if disperse cancer cells exist in the suspect mass some of those cancer cells will be captured in the samples. Each time the device is placed the physician must locate and direct the device with ultrasound imaging into the correct position near the suspect mass. Some breast tumors and lesions are very well defined, hard spherical masses which grow within the soft, compliant breast tissue. It is difficult to force a needle into these lesions because they are resistant to puncture and fairly mobile. Forcing the biopsy needle into the lesion is like trying to spear an apple floating in water.

Vacuum assisted biopsy system proposed by Biopsys involves sucking a breast lesion into a cannula and shearing off the captured edge of the lesion to obtain a biopsy sample. The device uses a vacuum to collect tissue into the side of an open tubular device, and then uses a rotating corer to cut the tissue collected. The rotating corer is slidable within the tubular section and can be pulled back to remove the tissue collected in the rotating corer. An additional stylet inside the rotating corer can be used to push the tissue out of the corer. The device can be rotated on its axis to remove a sample, 360 degrees around the central placement of the device. Typically, physicians sample six to eight cores. One advantage of this device is that the physician does not have to remove the device for additional biopsy samples. However, the tumor itself must be re-engaged after every coring operation, which entails substantial effort in relocation and confirmation that the target suspect mass has been engaged by the side aperture. Tumors may be too tough to yield to the suction and deform as necessary to enter the side opening of the cannula. Doctors also currently use the device to take a circular sequence of cores by rotating the device about its long axis or by sideways movement of the suction head to take a line of cores.

After biopsy and analysis, the tumor must be treated with a separate device, as Biopsys teaches that their coring device should not be used for resection. Indeed, the device is not designed to perform resection with assurance that complete resection of a suspect mass has been accomplished. Mechanical cutting and disruption of the tissue structure and cancer cell dispersion (that is, tearing of the tissue around the cancer and movement of the cancer cells amongst normal tissue) will result in unintentional delivery of cancer cells into healthy tissue adjacent the lesion.

SUMMARY

The device described below provides for diagnosis of tumors within the breast. The device includes an adhesion probe with structures that permit the surgeon to secure a suspect mass or tumor within the breast during the biopsy procedure. The probe is provided with a rigid tube and a sharp distal tip. To secure the tumor to the probe, the surgeon pierces the tumor with the distal rod. Tubing extending within the rigid tube directs coolant to the distal tip to cool the tip, the tumor then adhering to the cooled probe.

The device also includes a coring apparatus with structures that permit the surgeon to core a sample of the tumor during the biopsy procedure. The coring apparatus is provided with an outer cutting cannula that advances through a tumor to core a sample of the tumor. The coring apparatus is adapted for use with the probe. The adhesion probe is disposed within the cannula with the distal tip of the probe extending beyond the distal tip of the cannula. The device is inserted into the body until the adhesion probe pierces the tumor. Coolant is directed to the distal tip of the probe to lightly cool the distal tip and the tumor. The lightly cooled distal tip adheres to the tumor cells immediately proximate the distal tip. Once the tumor is secured to the probe, the coring apparatus is actuated to excise tumor tissue surrounding the distal tip. The coring apparatus comprises a cutting cannula and means for rotating and translating the cutting cannula. After coring is complete, the device is removed from the body and the cutting cannula is retracted to release the excised tissue. This method of biopsy prevents destruction of the tumor cells and reduces seeding (the dispersion of tumor cells to healthy cell areas).

Small canisters of $CO_2$, (carbon dioxide) or $N_2O$ (nitrous oxide), sometimes referred to as whippets, provide the coolant to the device. These small canisters eliminate the need for hoses remotely connected to large coolant canisters and allow the surgeon to freely operate during a procedure without the possibility of severing or tangling coolant supply tubes. The use of liquid $CO_2$ facilitates rapid yet moderate freezing of the target tissue lesion proximate the adhesion probe. The larger heat capacity of the liquid cryogen, vis-à-vis gaseous cryogen such as Argon gas, allows for further miniaturization of the reservoir and cooling probe components, with an overall gain of cooling efficiency and faster cooling operation. The liquid $CO_2$ is also used to drive the rotation and longitudinal translation of the biopsy coring apparatus. The system is controlled with various electromechanical interlocks and a microchip programmed to operate the system in response to operator input and various predetermined parameters.

DETAILED DESCRIPTION OF THE INVENTIONS

Figure 1:
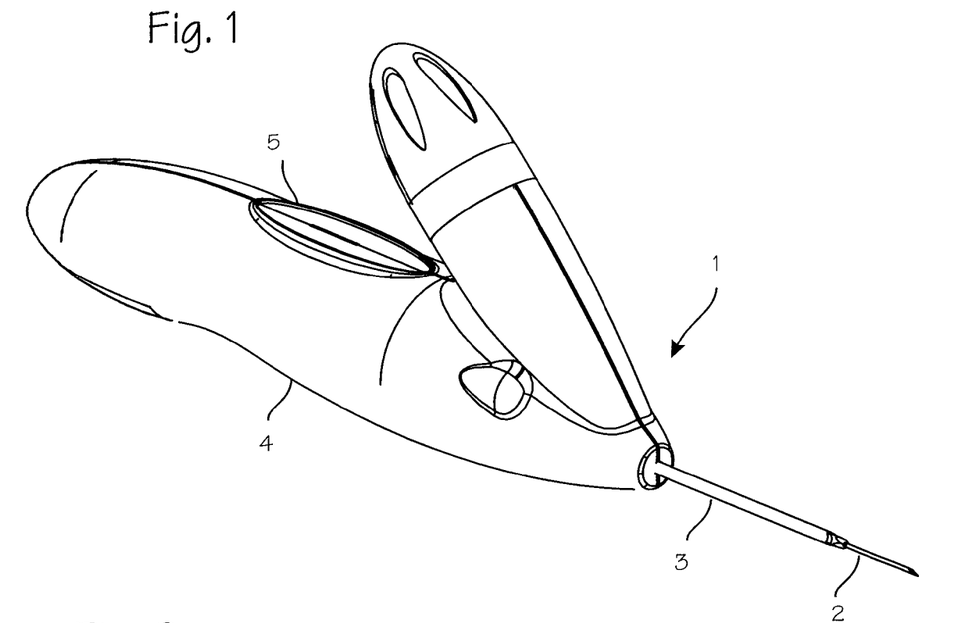
FIG. 1 is an isometric view of the biopsy instrument.

FIG. 1 illustrates a biopsy instrument 1 which comprises an adhesion probe 2, a cutting cannula 3, and a housing 4 sized and shaped to form a convenient handle and also to house the components of the instrument. The housing further comprises a button interface 5, detailed in FIG. 2, which allows the user to control the device and which reports to the user the state of the device. The button interface comprises a sample button 6 which may be depressed by the user to initiate sampling operation of the device, a retract button 7 which may be depressed by the operator to initiate retraction of the cutting cannula after sampling, a ready light 8 which is operable by the device controller to indicate to the operator that the device is ready for use, a sample light 9 which is operable by the control system to indicate that the device is operating to core a biopsy sample from a patient, and an expended light 10 to indicate when the $CO_2$ liquid has been expended. Membrane switches, or any other form of input device may be used as input buttons. The indicator lights may be replaced with any form of visual, audible, or tactile indicator capable of providing several distinct signals to the user.

Figure 3:
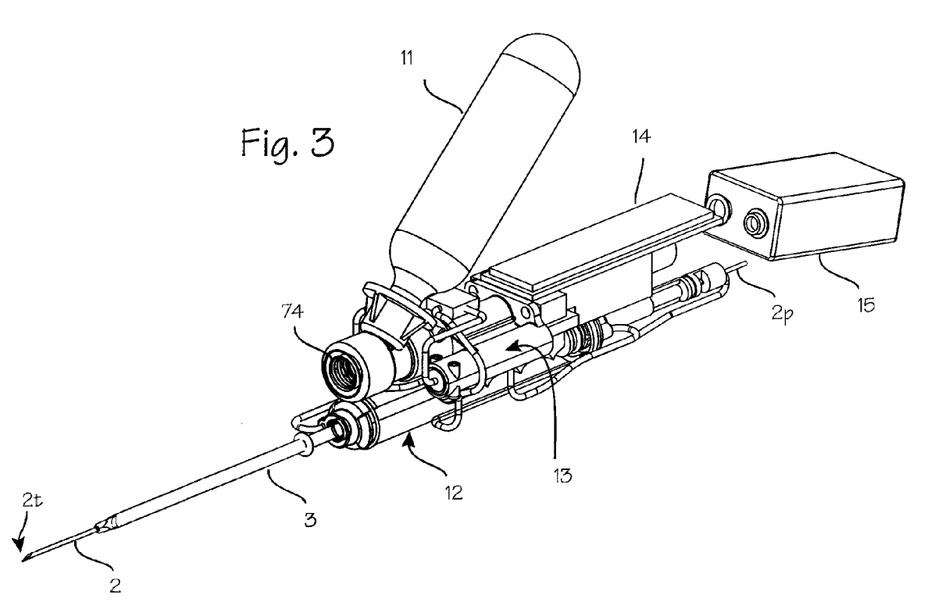
FIG. 3 is an isometric view of internal components of the biopsy instrument illustrated in FIG. 1.

FIG. 3 is an isometric view of the internal components of the biopsy instrument illustrated in FIG. 1. The adhesion probe 2 and cutting cannula 3 are operably connected to the various components illustrated in FIG. 3. Coolant is supplied to the adhesion probe from the small portable liquid $CO_2$ canisters or whippets 11. Canisters of $N_2O$ (nitrous oxide), ethane, propane, methane or tetrafluoromethane (R14) may also be used. Because the device is designed to use the liquid cryogen, rather than the gaseous cryogen, within the canister, the canister is held in fixed relationship to the biopsy instrument, with the outlet pointing downward, establishing an up-and-down orientation for the device. In use, the canister which is disposed at a substantial angle relative to the adhesion probe is disposed in an inclined position when the adhesion probe is horizontally oriented.

The biopsy instrument includes a coring mechanism that serves as both a translating mechanism and a rotating mechanism for the cannula. As illustrated, the translating mechanism and a rotating mechanism are provided in the form of a combined translating/coring mechanism which performs the rotating operation as it performs the longitudinal translation of the cannula that is required for coring. The combined translating/coring mechanism is comprised of a hydraulic actuator 12 and the various valves in valve block 13 and mechanical components described in more detail below. A computerized control system is provided on a printed circuit board 14. The control system is powered by a 9 volt battery 15 or other suitable power source. The battery can be removed if needed to facilitate disposal.

FIGS. 3, 4, 5 and 6 show various views of the biopsy instrument, which is adapted for use with an adhesion probe 2 for securing a breast tumor during a biopsy or resection procedure. A suitable adhesion probe is described in Van Bladel, et al., *Device for Biopsy of Tumors*, U.S. Pat. No. 6,551,255 (Apr. 22, 2003), incorporated herein by reference. The adhesion probe 2 comprises a long, slender yet rigid tube. A short rigid penetrating segment 2d extends distally from the distal end of the rigid tube, and a coolant inlet tube passes through the rigid tube, extending to the distal end of the rigid tube, and terminating just proximal of the distal tip of the penetrating segment. The distal tip 2t is beveled, and the bevel face is oriented to face upward relative to the device, and thus is radially aligned with the cryogen canister, so that it is oriented superficially, toward the skin of the patient, when in use. The cutting cannula 3, also described in Van Bladel, is slidably disposed around the adhesion probe, longitudinally translated relative to the adhesion probe and adapted for insertion through a small incision in the skin, and may be inserted along the with the adhesion probe or over the adhesion probe. The cutting cannula may be forced distally over the penetrating segment 2d to core any tissue which is secured to the penetrating segment from any surrounding body tissue.

Figure 4:
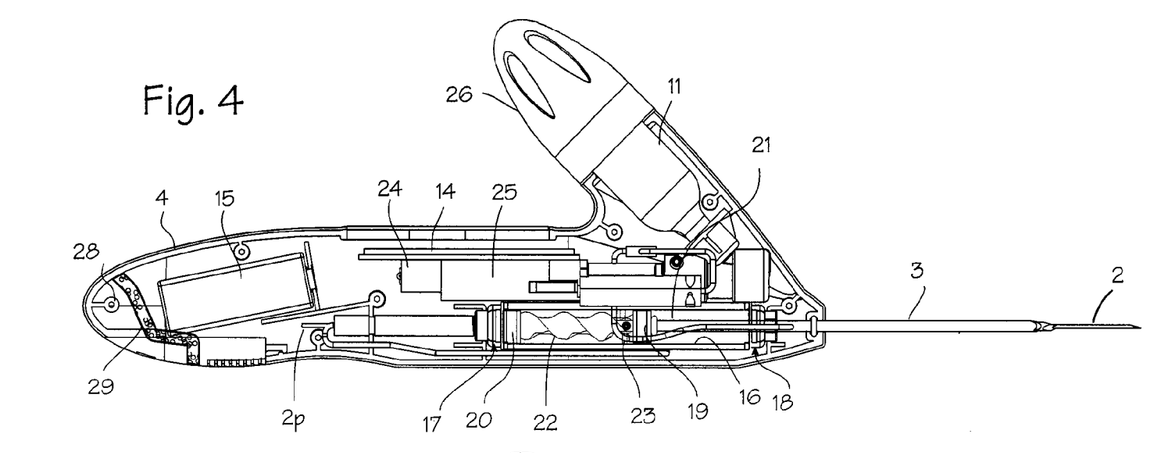
FIG. 4 shows a cross-sectional view of the biopsy instrument with the cutting cannula in the retracted position.
Figure 5:
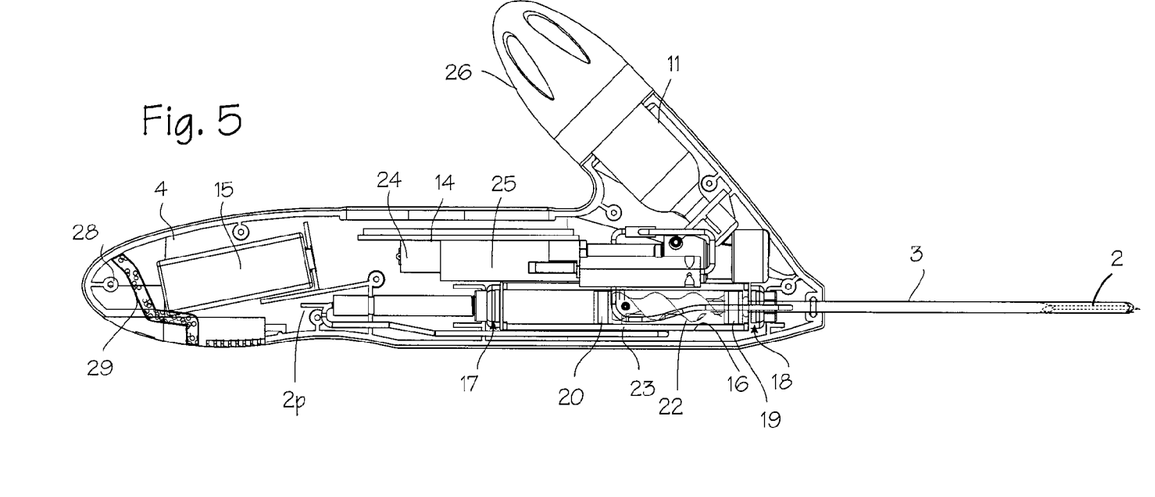
FIG. 5 shows a cross-sectional view of the biopsy instrument with the cutting cannula in the advanced position.

As illustrated most clearly in the side views of FIGS. 4 and 5, the actuator 12 includes a cylinder or piston chamber 16, a proximal closure head 17 and a distal closure head 18, a proximal piston 19 and a distal piston 20, lead screw or jackscrew 21 disposed between the proximal and distal pistons, and an actuator rod 22. The lead screw is bounded on both sides by the pistons 19 and 20. The cylinder 16 can be formed from the inner surface of the housing, or the housing may be integrally formed with the cylinder. The pistons are disposed within the piston cylinder chamber, such that the pistons, although tightly fitting within the cylinder chamber, are capable of translating longitudinally along the cylinder. They may also be rotatable relative to the cylinder.

The pistons are attached to the cannula 3, and are longitudinally fixed to the cannula, through the actuator 22. The actuator may be integrally formed with the cannula, and may, as illustrated, be formed of the proximal extent of the cutting cannula. The pistons may be rotatably fixed to the cannula, but the cannula may also be longitudinally fixed to the pistons while remaining freely rotatable relative to the pistons. The translation of the pistons distally and proximally through the cylinder is translated to the cannula. The actuator rod or proximal extent of the cannula may extend from the proximal end of the housing, through a bore in the proximal piston and the distal piston, and through the lead screw 22, or it may terminate proximally at the distal piston, or any point in between, so long as it is fixed to the pistons.) In the embodiment shown, the adhesion probe and cannula are coaxially disposed within the pistons, actuator rod and cylinder.

The cannula rotating mechanism is comprised of a lead screw 22 (which also serves as the actuator rod) and a lead screw nut 23. The lead screw is formed of a tube, with screw threads on the outside of the tube and a lumen passing through the tube. The lead screw is longitudinally fixed to the pistons, such that the lumen of the lead screw communicates with the respective piston bores. (The actuator rod or proximal extent of the cannula may pass through the lumen of the lead screw.) The lead screw nut is adapted to receive the lead screw. The lead screw is screwed into and through the lead screw nut. The cannula 3 is rotationally fixed into the lead screw, either directly or indirectly. When the pistons are translated, the lead screw translates under operation of the pistons and rotates via translation of the lead screw through the lead screw nut. The lead screw can have a pitch of 1 inch per revolution, such that for every inch of translation, the lead screw rotates one revolution. Because the lead screw is rotationally fixed to the cannula, the rotation of the lead screw is translated to the cannula.

The cannula translating mechanism has a retracted/proximal position and an extended/distal position. FIG. 4 illustrates the translating mechanism in the retracted position, where the cannula 3 will not be engaged with the tumor. In the retracted position, the distal piston is positioned at the proximal end of the cylinder and the penetrating segment 2d of the adhesion probe 2 is exposed, extending distally from the cannula. FIG. 5 illustrates the translating mechanism in the advanced position, with the cannula translated distally over the penetrating segment 2d of the adhesion probe, where it will engage and core a tumor secured to the penetrating segment. Comparison of FIGS. 4 and 5 illustrates the cooperative interaction between the proximal and distal pistons, the lead screw, and the cutting cannula. FIGS. 4 and 5 also show the $CO_2$ canister 11, the valve block 13, the computerized control system 14, the battery 15, the motor 24, and the gear box 25, all within the housing 4. The $CO_2$ canister 11 is shown disposed within the vertically oriented canister housing (formed integrally with the housing 4) and is held in place by the screw-cap 26. The outlet of the $CO_2$ canister is jammed into the pierce pin connector 27 upon closure of the screw-cap, establishing a fluid pathway from the canister to the valve block. The $CO_2$ used in the probe exhausts from the proximal end 2p of the adhesion probe, and thence through exhaust vent 28 in the device housing, shown in FIGS. 4 and 5. A filter 29 is disposed in the exhaust gas pathway to prevent cryogen from escaping (small bits of solid $CO_2$, or droplets of liquid $N_2O$, may be ejected from the proximal end of the adhesion probe).

Figure 6:
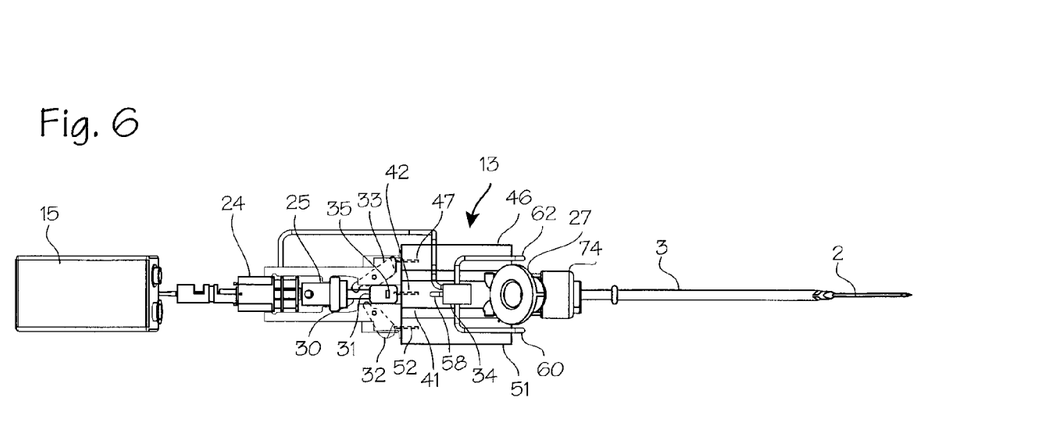
FIG. 6 shows an elevated cross-sectional view of the biopsy instrument.

FIG. 6 shows a top view of the biopsy instrument, in which the valve block 13 and gear motor 24 are more clearly visible. The main valve 41, advance valve 46 and retract valve 51 are connected through various tubes which direct fluid flow to the various components, as described in relation to FIGS. 7a through 7d. The motor is shown at the proximal end of the instrument, proximal of the valve block 13. The motor is operably connected to the various valve stems (see FIGS. 7a through 7d) through motor gear box 25, jack screw 30 and the jack screw nut 31 (also referred to as a drive nut). The drive nut operates directly on the main valve stem 42, and operates the advance valve stem 51 through cam 32, and operates on the retract valve stem 47 through cam 33. Proximal movement of the jack screw nut results in operation of cam 32 to impinge on advance valve stem 51 to open the advance valve an direct flow of high pressure liquid cryogen to the advance side of the cutter actuator piston, and further proximal movement of the jack screw nut results in rotation of cam 33 to impinge on retract valve stem 47, pushing the retract valve stem into the retract valve to open the valve and direct flow to the retract side of the cutter actuator piston.

A manifold 34 is used to distribute liquid cryogen from the main valve to the various points in the system. Main valve outlet tube 58 provides a fluid pathway from the main valve to the manifold, and the fluid is then distributed to the retract valve through retract valve supply tube 62 and to the advance valve through the advance valve supply tube 60. The small wiper contact 35 on the drive nut interacts with a corresponding trace on the printed circuit board which is fixed in predetermined position relative to the valve stem such that the wiper/trace combination may act as a limit switch to provide feedback to the computer control system as to the position of the drive nut and main valve stem. This trace and/or additional traces on the circuit board can be used as described below to provide feedback for control of the motor and drive nut.

FIGS. 7a through 7d are schematic diagrams of the valve assembly and associated tubing for operating the biopsy instrument of FIG. 1. The valve assembly comprises the valve block 13, which includes a main valve and two associated valves which have inlets aligned to the outlet of the main valve. The main valve 41 comprises a main valve stem 42, main valve outlet 43, main valve inlet 44 and main reservoir 45. The retract valve 46 comprises a retract valve stem 47, retract valve outlet 48, retract valve inlet 49 and retract reservoir 50. The advance valve 51 comprises an advance valve stem 52, advance valve outlet 53, advance valve inlet 54 and advance reservoir 55. The valves are spring loaded plunger valves which are normally closed, such that movement of the plunger into the valves opens the valves. The valves may comprise a ball which is forced against the valve seat, or a typical plunger valve with a seal positively fixed to the plunger, as shown. The inlets of both the retract valve and the advance valve are fitted with check valves 56 and 57, which may be spring biased ball check valves or any other type of check valve.

Figure 7A:
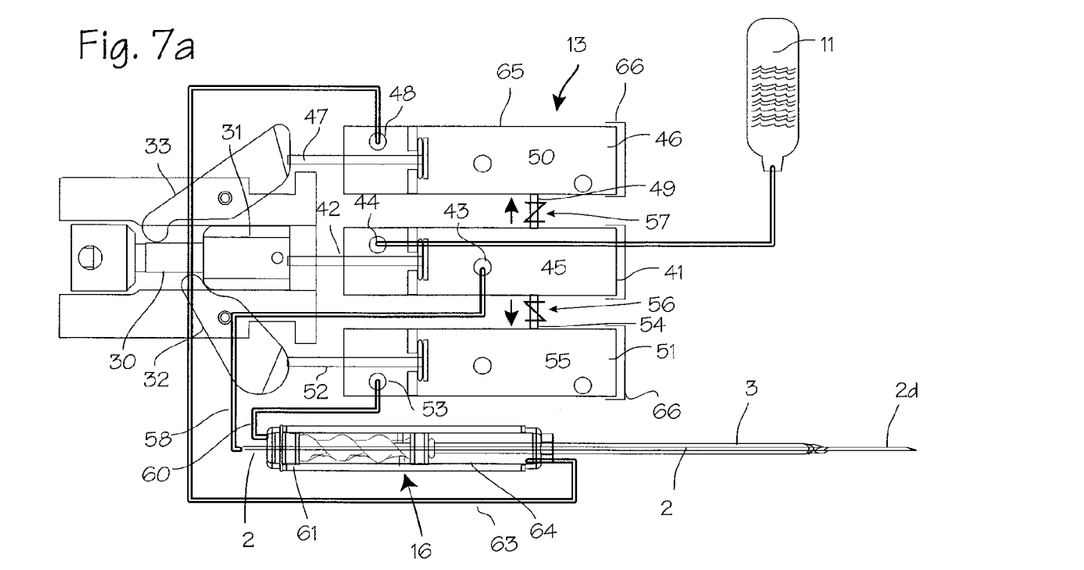
FIGS. 7a, 7b, 7c and 7d are schematic diagrams of the valve assembly and associated tubing for operating the biopsy instrument of FIG. 1.

FIG. 7a shows the system in its initial condition, with all three valves closed, the cutting cannula in the retracted position, and the adhesion probe extending distally from the distal extent of the cutting cannula. The $CO_2$ canister is filled with liquid $CO_2$, and is in fluid communication with the inlet of main valve 41.

Figure 2:
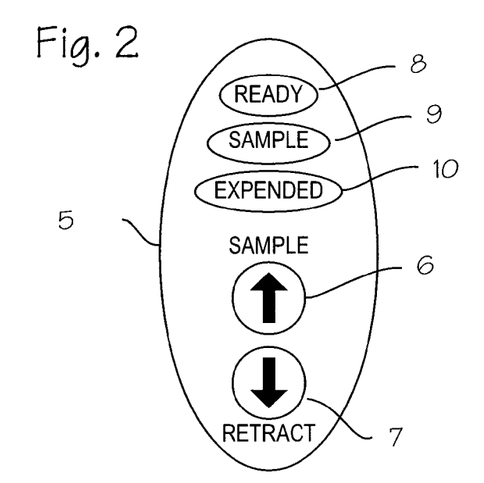
FIG. 2 illustrates the user interface of biopsy instrument illustrated in FIG. 1.
Figure 7B:
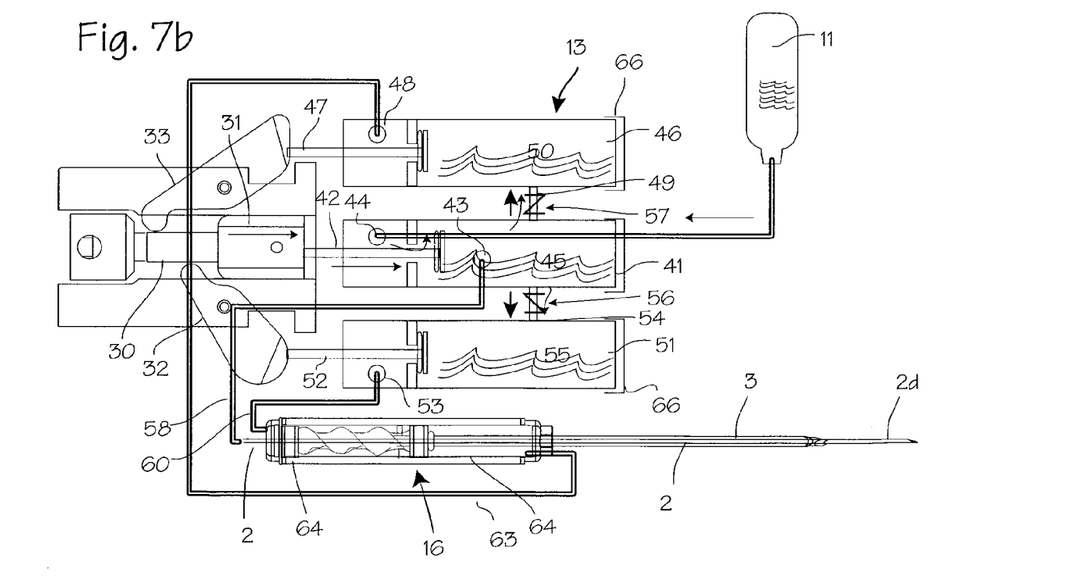

During sampling operation (which is initiated when the user depresses the sample button on the input pad shown in FIG. 2), the motor (item 24 in FIG. 6) operates through linkages to drive the jack screw nut forward, thus driving the main valve stem 42 forward, thereby opening the main valve, as shown in FIG. 7b. The main valve is driven forward from a home position until the electrically conductive wiper that is mounted to the drive nut loses contact with traces on the printed circuit board (any other form of contact switch, proximity switch, encoder or sensor may be used to sense the position of the main valve stem (and, thus, the state of the valve)). The motor stops in this position for a period (the dwell time) which may be predetermined or calculated by the computerized control system. Preferably, the dwell time is calculated by the control system based on the time required for the conductive wiper to traverse the trances on the printed circuit board. This dynamic calculation of the dwell time allows the computerized control system to automatically compensate for variations in the sped of the valve stem travel due to motor characteristics, friction in the system, and battery voltage. With the main valve open, liquid $CO_2$ flows through the main valve outlet 43 to the coolant supply tubing 58 that is connected to the adhesion probe 2. (The sample light 9 is flashed while cryogen is flowing to the adhesion probe to indicate to the operator that the device is operating in cooling mode. Other distinctive indications may be provided to the operator.) As the cryogen exits the port inside the adhesion probe 2, the temperature of the penetrating segment 2d drops. While liquid is flowing to the adhesion probe, liquid is also routed to charge the advance reservoir 55 and retract reservoir 50 through the advance valve inlet 54 and the retract valve inlet 49. The size of the reservoirs are calculated to provide a set pressure inside the cylinder once all of the valves open and the liquid $CO_2$ is turned to vapor with an expansion ratio of 400:1 or more (compensating for end state gas temperature).

Figure 7C:
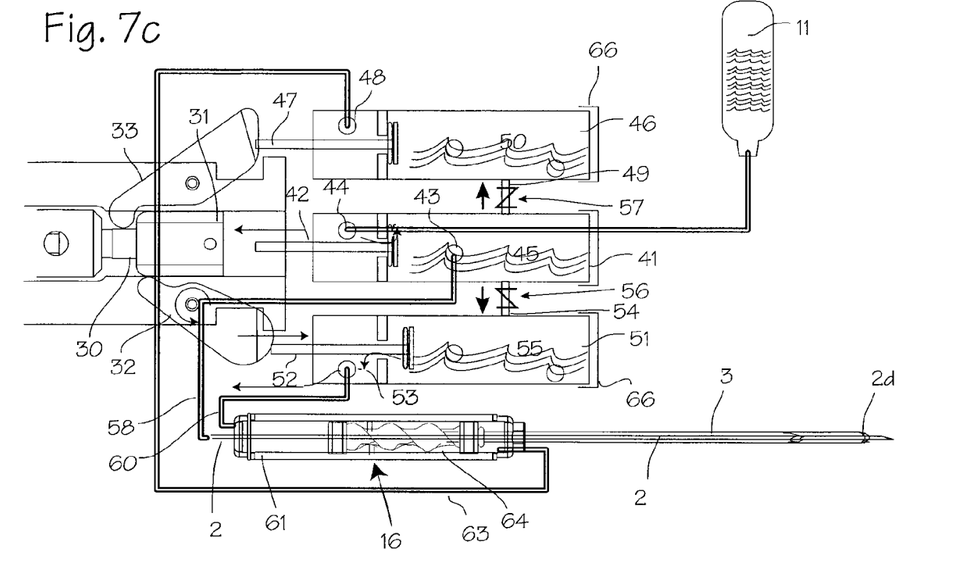

After the dwell time, the motor is reversed. As the main valve stem 42 moves backward, as shown in FIG. 7c, the main valve closes. The motor continues in reverse operation to drive the drive nut backward. At this point, the main valve is fully closed and the cooling flow to the adhesion probe ceases. The jack screw nut 31 encounters a cam 32 and forces the cam to pivot forward and forces advance valve stem 52 forward to open the advance valve 51. This allows fluid to flow through the pressure tubing 60 into the advance side 61 of the piston cylinder 16 which drives the cutting cannula forward. As the cannula translates, the cannula rotates under operation of the lead screw and lead screw nut assembly illustrated in FIGS. 4 and 5. Any tissue stuck to the tip of the adhesion probe when the cannula is translated and rotated is cored from the surrounding lesion. The motor continues in reverse operation to draw the drive nut backward until the wiper encounters a second contact (the second contact is located on the circuit board or other fixed structure located above the drive nut) and stops. The cutting cannula is fully extended over the adhesion probe, and has excised any tissue adhered to the distal segment of the adhesion probe. The time required for this complete stick freeze/advance cycle is preferably less than 10 seconds, and is about 4 seconds using the embodiments illustrated. The control system illuminates the sample light 9 on the input pad continuously after advancing the cutter, to indicate to the operator that the coring operation is complete.

Though the electromechanical valve actuators described above in relation to FIGS. 6 and 7a through 7d provide for fairly simple, compact and quick actuation of the valves in the high pressure system, other electromechanical valve actuators may be used. Each valve may be driven by a different solenoid actuator or a different motor, and each actuator or motor may be operated by the control system programmed to provide the valve timing described above. Other valve actuators, including pneumatic actuators (driven by the high pressure cryogen stored in the canister), shape memory actuators (heated by the battery, as controlled by the control system), and any other valve actuating means may be used. The embodiment described above, however, is compact, sufficiently powerful to operate against the high pressures of the cryogen, and inexpensive.

Figure 7D:
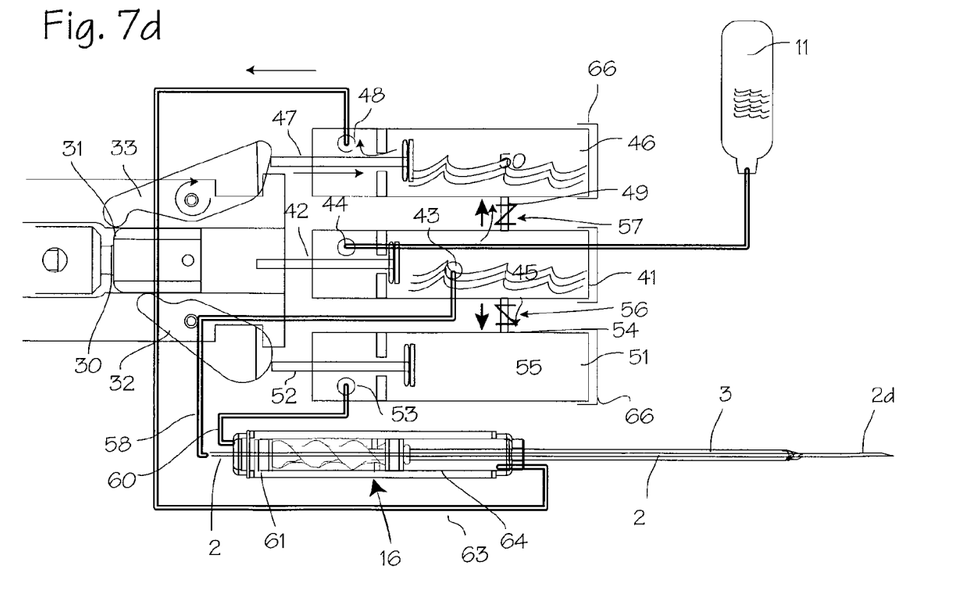

During retraction (which is initiated when the user depresses the retract button 7 on the input pad shown in FIG. 2) the control system operates the motor continues to operate, in reverse, to move the drive nut backwards until a second cam 33 is encountered by the jack screw nut 31. This second cam pivots forward and opens the retract valve 46, as shown in FIG. 7d. This allows fluid to flow through the pressure tubing 62 into the retract side 63 of the piston cylinder, which in turn retracts the cutting cannula. The tissue excised from the body is then exposed, and is readily removed from the distal segment of the adhesion probe.

The advance side 61 of the piston cylinder 16 must be evacuated prior to application of high pressure fluid to the retract side, to prevent hydraulic/pneumatic binding of the piston. The advance side of the piston cylinder may be vented in any convenient manner. In the device illustrated in the Figures, the valve bodies comprise cylinders 65 with end caps 66. The threading of end cap on the advance valve is machined so that it is slightly loose (or gas valve threads are used, and the cap is not completely seated) and allows slight leakage of the cryogen from the valve body reservoir. Thus, after the bulk of the cryogen is exhausted into the piston cylinder the advance side exhausts through the end cap. The retract cylinder is vented in the same manner. Vented may be accomplished with small apertures in the end caps or valve bodies in similar fashion.

The amount of time in which coolant is flowing depends on desired temperature of adhesion probe. Final temperature of about −3° to −20° C. is desired for biopsy, while a final temperature below −30° C. is desired for cryo-preservation. Alternatively, a thermocouple may be embedded in the adhesion probe so that the device may be temperature controlled rather than time controlled. This will compensate for differences in device or tissue thermal loading, or the difference between the first shot of liquid $CO_2$ and the last as the device cools down, and for variations in the speed of the valve stem travel which may result from variations in the battery. For a standard biopsy with a fully charged battery, the dwell time after the main valve is fully open is about 0.5 to 2.0 seconds. The valve is open, then, for about 5 seconds, which includes the dwell time and the time in which the valve stem is moving (and the valve is open). $CO_2$ flow of 0.05 and 1.25 grams per 5 second cycle (0.01 to 0.25 grams per second) provides adequate cooling for biopsy, which requires cooling sufficient to adhere the probe to the tissue, and preferable does not result in extensive freezing. This flow is appropriate in embodiments in which the adhesion probe outer tube has an outer diameter of 0.0.43 inches and an inner diameter of 0.029 inches (a 19 gauge hypo tube), and the adhesion probe inner tube has an outer diameter of 0.020 inches and an inner diameter of 0.007 inches (28 gauge). The flow rate may be adjusted as necessary with different constructions of the device.

After moving the jack screw nut back a set distance, the motor is stopped and then driven forward until the jack screw nut is driven to its home position. The control system checks the battery voltage and verifies that the number of cycles used is within the capacity of the $CO_2$ canister. Conveniently sized canisters hold enough liquid $CO_2$ to supply the system for about 7 coring operations. Twelve to sixteen grams of liquid are sufficient in a canister filled to 75% density. If there are any cycles left, the ready light 8 illuminates. If not, the expended light 10 illuminates and the system is software disabled. The system will not operate if it has already counted 7 operating cycles (this limit is somewhat arbitrary, chosen to provide ample cycles for a single patient use, and it may be adjusted as manufacturers and doctors gain experience with the device).

Figure 8:
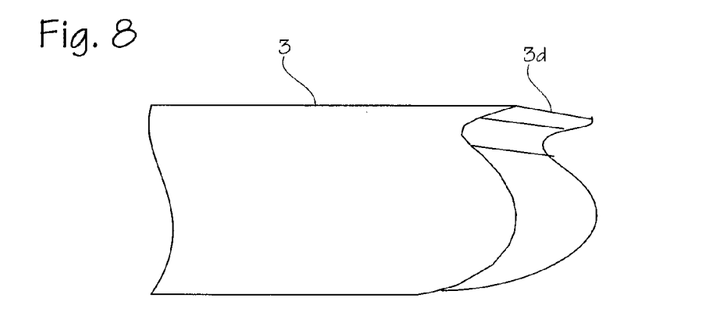
FIG. 8 shows a detailed view of the cutting cannula.

FIG. 8 shows a detailed view of the cannula cutter. The cutting edge is provided in the form of a scalloped bevel, formed by multi-axis machining. Thus, the cutting edge 3d has several distally extending, longitudinally rounded protrusions which are provided with a sharp longitudinally oriented bevel, with the cutting edge toward the inner wall of the cannula, and the bevel extending proximally toward the outer wall, and the circumference of the bevel following a scalloped or sinusoidal curve relative to the longitude of the cannula. A beveled tip with three such longitudinally rounded protrusions works well on breast tissue.

Figure 9:
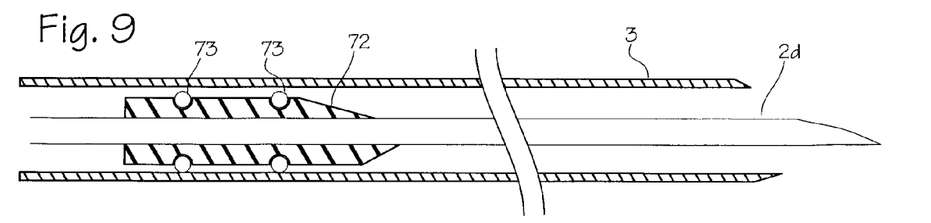
FIG. 9 illustrates details of the cutting cannula and adhesion probe.

FIG. 9 illustrates details of the cutting cannula and adhesion probe. The adhesion probe 2 and cutting cannula 3 of the prior figures are shown in cross section. A ferrule 72 is fitted coaxially over the adhesion probe, between the adhesion probe and the cutting cannula. The ferrule is fixed to the adhesion probe, and has an outer diameter closely matching the inner diameter of the cutting cannula, and is used to provide the proximal segment of the adhesion probe with a larger outer diameter than the distal segment. A trocar-type blade or tapered cone provides the transition from the outer diameter of the ferrule to the distally extending penetrating segment 2d is formed in. One or more ring seals 73 are disposed between the ferrule and the cutting cannula, and may be secured within annular grooves within the ferrule, as shown. The ring seals serve to prevent body fluids seeping into the clearance between the adhesion probe/ferrule and the cutting cannula and freezing during operation of the device, and this eliminates any interference with cannula translation that may result.

In use, the user screws down the screw cap 26. This drives the $CO_2$ canister 11 down into the pierce pin connector 27. When the canister is fully seated, an electrical connection is completed which "wakes up" the control system on the printed circuit board. A self-check program executes and exercises the gear motor 24 (shown in FIG. 6) to establish a home position. The time that it takes to move the main valve stem 42 (shown in FIG. 7a) from point to point is also measured and the valve cycle time is altered based on the measured speed to achieve a desired cryogen flow cycle time. An exemplary calculation would be:

valve cycle time=(desired cryogen flow cycle time)+ (valve stem travel time to initiate flow);

where desired cryogen flow cycle time=valve stem travel time after valve opening+dwell time.

In each case, the valve stem travel time is calculated by dividing the distance the valve must travel (which depends on the construction of the device) by the measured speed of the valve stem (which corresponds to the speed of the drive nut). The speed of the drive nut is determined by measuring the time required to travel past the trace, or to move from one trace to another trace, given that the trace(s) are fixed relative to the drive nut wiper and the length of the trace (or the distance between the traces) is known.

After a successful self-check, the ready light 8 on the button interface 5 illuminates. The user, typically a surgeon or radiologist, inserts the distal tip of the adhesion probe into a tumor or other suspect mass within the body of a patient. When the user is satisfied with the position of the adhesion probe, the user depresses the sample button on the input pad, and the system initiations the cooling and coring operation described above in relation to FIGS. 7a through 7c. After the coring operation is complete, the control system operates the sample light continuously to indicate to the operator that the sample has been cored from the patient. The user than removes the probe from the patient, and depresses the retract button on the input pad. In response, the control system initiates the retraction operation described above in relation to FIG. 7d. The cored tissue sample may then be removed from the distal tip, and, if the user desires to take more samples, the adhesion probe can be re-inserted into the body.

The system is provided with safety features to prevent over-pressurization, initiation of sampling with a partially discharged device, etc. The average pressure inside the $CO_2$ canister at room temperature is 850 psi. Extreme ambient heating may result in canister pressure of 3 kpsi. The burst pressure of the canister is 10 kpsi, but there is no need to construct the entire probe to withstand such high pressure. Thus, a burst disk 74 (shown throughout the figures) may be placed in line with the main valve so that it will vent when the pressure is higher than 3 kpsi. Any other suitable pressure relief means may be used. In the event the probe, after having a canister installed, is set aside for an inordinately long time, the canister may self discharge, so that it no longer hold enough gas for a full compliment of sampling procedures, or doctors may inadvertently attempt to use a device on a patient after it has already been used on another patient. Thus, the control system is programmed to exhaust the probe after a predetermined time period, such as by driving the drive nut forward to vent out any remaining gas. Thus, the chance of initiating sampling with a partially charged device that may have been used with another patient is minimized. Additionally, the device is provided as a disposable device, such that it cannot be recharged and re-used. This is accomplished with appropriate programming of the computerized control system within the device. The device could be sent back for re-processing, however, in which case the circuitry, internal components and housing can be recycled into new devices with sterile probe and cutter assemblies, and the control system could be reset to allow another set of operating cycles.

While the preferred embodiments of the methods have been described in reference to the environment in which they were developed, they are merely illustrative of the principles of the inventions. Other embodiments and configurations may be devised without departing from the spirit of the inventions and the scope of the appended claims.

We claim:

1. A system for securing a mass within the breast of a human patient, said system comprising:
    a coring mechanism comprising: a cryogenic adhesion probe comprising a tube adapted for insertion into the body of the patient, said tube having a proximal end, a distal end, a proximal segment, and a distal segment, said proximal segment having a larger outer diameter than the distal segment; said distal segment having a penetrating element adapted for piercing the mass;
    a cutting cannula disposed about the tube, said cutting cannula characterized by a proximal end and a distal end, said cutting cannula having an inner diameter larger than outer diameter of the distal segment of the adhesion probe;
    a fluid actuator comprising a first piston slidably disposed within a cylinder, a first chamber on one side of the first piston and a second chamber on the other side of the first piston, said first piston being longitudinally fixed to the cutting cannula; a
    rotating mechanism comprising a lead screw and a lead screw nut adapted to receive the lead screw which comprises a tube with screw threads on the outside of the tube and a lumen passing through the tube wherein the lead screw is longitudinally fixed to the pistons such that the lumen of the lead screw communicates with the respective piston bores and wherein the cannula is rotationally fixed into the lead screw; and
    a housing integrally formed with the cylinder that is sized and shaped to form a handle comprising a control system, a battery, a button interface adapted to allow a user of the system to control the system and adapted to report to the user the state of the system, and a canister of liquefied gas and means for selectively supplying liquefied gas from the canister to the adhesion probe, the first chamber and the second chamber;
    wherein the canister is disposed at a substantial angle relative to the adhesion probe, whereby the canister is disposed in an inclined position when the adhesion probe is horizontally oriented and wherein the housing contains the coring mechanism.

2. The system of claim 1 wherein the means for selectively supplying liquefied gas further comprises:
    a first valve with and input connected to the canister and an output connected to the adhesion probe;

a second valve having an input connected to the outlet of the first valve and an output connected to the first chamber;

a third valve having an input connected to the outlet of the first valve and an output connected to the second chamber; and valve operating means for selectively operating the first valve, second valve, and third valve.

3. The system of claim 2 wherein the cutting cannula is a scalloped bevel, formed by multi-axis machining.

4. The system of claim 2 wherein the button interface comprises a sample button which may be depressed by the user to initiate sampling operation of the system, a retract button which may be depressed by the user to initiate retraction of the cutting cannula after sampling, a ready light operable by the system controller to indicate to the user that the system is ready for use, a sample light operable by the control system to indicate that the system is operating to core a mass from a patient, and an expended light to indicate when the liquefied gas has been expended.

5. The system of claim 2 wherein the control system is operable to operate the valves.

* * * * *